United States Patent [19]
Duncan et al.

[11] Patent Number: 5,133,771
[45] Date of Patent: Jul. 28, 1992

[54] FLEXIBLE MOLD FOR FORMING COMPOSITE OF A HIP REPLACEMENT COMPONENT AND A BONE CEMENT SLEEVE

[75] Inventors: Clive P. Duncan; Martine J. Breault; Christ P. Beauchamp; Nancy J. Paris, all of Vancouver, Canada

[73] Assignee: University of British Columbia, Vancouver, Canada

[21] Appl. No.: 670,905

[22] Filed: Mar. 18, 1991

[30] Foreign Application Priority Data

Dec. 5, 1990 [CA] Canada ................................. 2031571

[51] Int. Cl.$^5$ ............................ A61F 2/28; A61F 2/34; A61F 2/36
[52] U.S. Cl. ........................................ 623/23; 623/22; 623/18; 623/16; 606/60
[58] Field of Search .................. 623/16, 18, 23, 22; 606/76, 77, 65-68, 60, 62-64

[56] References Cited

U.S. PATENT DOCUMENTS

| | | | |
|---|---|---|---|
| 4,750,905 | 6/1988 | Koeneman et al. | 623/16 |
| 4,888,024 | 12/1989 | Powlan | 623/23 |
| 4,900,546 | 2/1990 | Posey-Dowty et al. | 623/16 X |
| 4,950,300 | 8/1990 | Langlais | 623/23 |
| 5,015,257 | 5/1991 | Crowninshield et al. | 623/18 X |

FOREIGN PATENT DOCUMENTS

| | | | |
|---|---|---|---|
| 0016480 | 10/1980 | European Pat. Off. | 623/23 |
| 0129531 | 12/1984 | European Pat. Off. | 623/18 |
| 2639820 | 6/1990 | France | 623/18 |

Primary Examiner—Randall L. Green
Assistant Examiner—D. Willse
Attorney, Agent, or Firm—C. A. Rowley

[57] ABSTRACT

A custom made femoral component is made using the femoral cavity and an internal latex envelope as the mold. After the femoral cavity is worked into a roughly conical shape, an internal latex envelope is inserted into the cavity and filled with bone cement. An endoskeleton is inserted down the femoral cavity into the bone cement. The internal latex mold conforms to the shape of the cavity and an accurate negative of the cavity is created as the bone cement solidifies. The femoral component is pulled from the cavity and the internal latex envelope is peeled off the component. All traces of the internal latex envelope is removed from the femoral cavity and component. The femoral component is then reimplanted.

11 Claims, 6 Drawing Sheets

PRIOR ART

FIG. 1

PRIOR ART

FIG. 2

PRIOR ART

FIG. 3

PRIOR ART

FIG. 4

PRIOR ART

FLEXIBLE MOLD FOR FORMING COMPOSITE OF A HIP REPLACEMENT COMPONENT AND A BONE CEMENT SLEEVE

INTRODUCTION

This invention relates to a method of treating an infected joint following total joint replacement. It also relates to a prosthesis and a method of manufacturing a prosthesis.

BACKGROUND OF THE INVENTION

Infection following a total joint replacement is an unavoidable complication affecting about 1.5% of patients resulting in an estimated 3,000 cases per year in North America alone. Eradication of the infection and the joint reconstruction, preferably by reimplantation of another joint, is important to a successful outcome.

Basically, three methods have developed in dealing with this problem. The first is excision of the joint, whereby the use of the limb is severely compromised.

Figure 1:
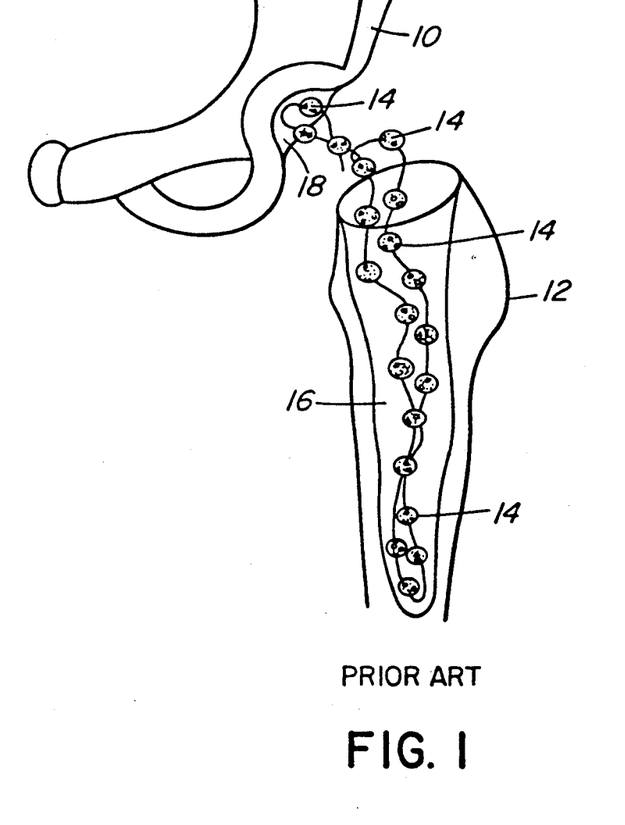
FIG. 1 shows a pelvic girdle and a femur and antibiotic loaded cement beads located in the femoral cavity or canal, as well as in the acetabular cavity, in the management of an infected total hip replacement according to a method which is known in the art.
Figure 2:
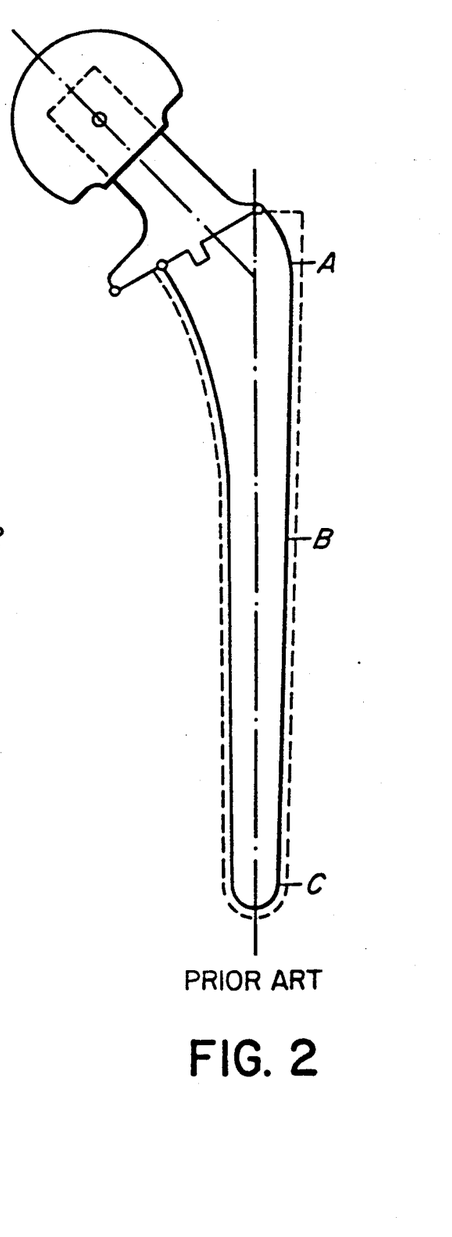
FIG. 2 is an anterior/posterior view of a femoral component of a permanent hip prosthesis which is known in the art, for use with cement.
Figure 3:
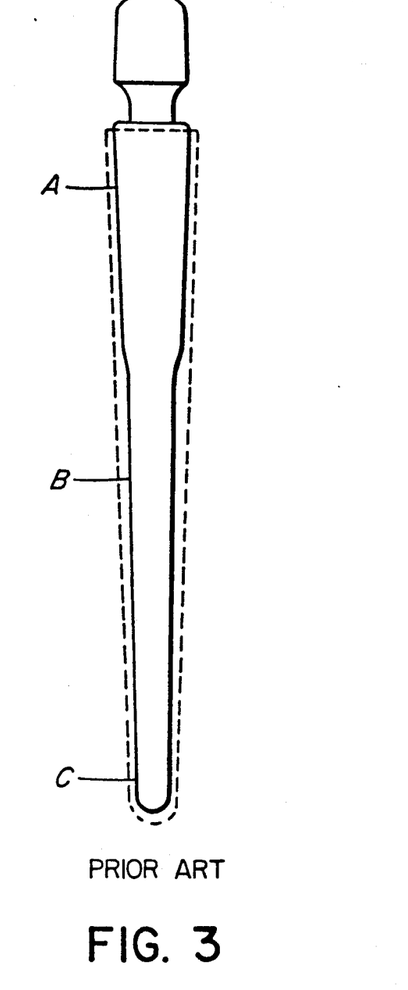
FIG. 3 is a lateral view of the femoral component of FIG. 2 with the femoral head omitted.
Figure 4:
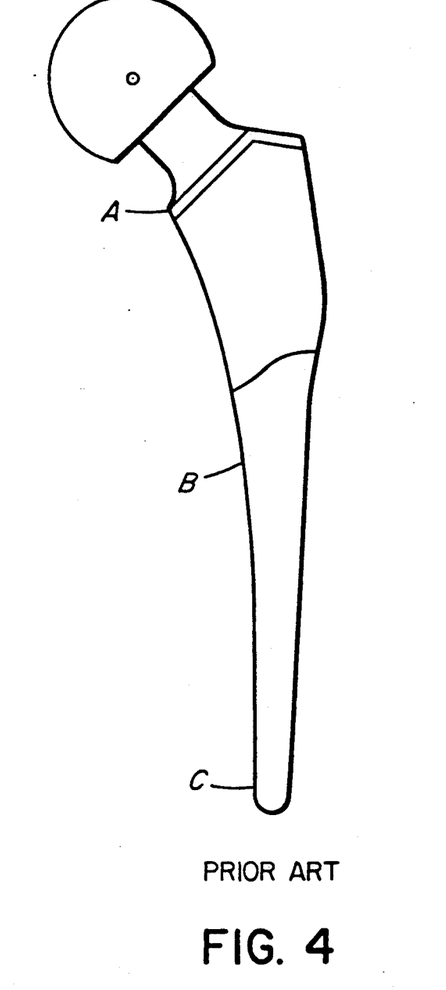
FIG. 4 is an anterior/posterior view of a femoral component of another permanent hip prosthesis which is known in the art, for cementless fixation.
Figure 5:
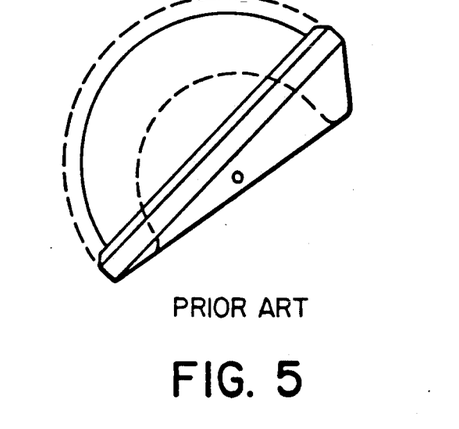
FIG. 5 is an anterior/posterior view of an acetabular cup which is known in the art and is intended for use with the permanent hip prosthesis of FIG. 2.

Secondly, there is a two-stage joint replacement revision. With this method, the existing hip replacement and all infected tissue is removed. Antibiotic loaded cement beads are placed in the femoral and acetabular cavities and left there for a period of six to twelve weeks until the infection has been eradicated. Once the infection has been removed, a new total hip replacement is implanted. The disadvantage of this method is that the patient does not have normal use of the limb during the interim period during which the infection is being treated. This situation is illustrated in FIG. 1 of the accompanying drawings, where a patient's pelvic girdle 10 and femur 12 are shown with antibiotic loaded cement beads 14 located in the femoral and acetabular cavities 16 and 18, respectively. Not only is the patient immobilized during this period but hospitalization is also necessary, resulting in high medical expenses.

The permanent prosthesis which is fitted after the infection has been removed is either cemented in position or it is applied without cementing by forming a press-fit with the femoral cavity. In the latter case, the stem of the femoral component is provided with a rough outer surface so that the bone can grow into the cavities on the surface to bind with the prosthesis. In the case of application of cement to the stem, the cement is compressed into the interstices of the femoral cavity to provide rigid fixation of the component.

The third method is a one-stage hip replacement by which a permanent prosthesis is fitted directly, without the intermediate step of the application of antibiotic loaded bone cement beads. In this application, the bone cement which is used to bond the permanent prosthesis in the femoral cavity contains an antibiotic. Thus, the permanent hip replacement is fitted directly after the existing hip replacement and infected tissue have been removed. The bone cement is applied to the stem of the prosthesis. The stem is then inserted into the femoral cavity for bonding in the cavity.

There is mounting scientific evidence that the two stage approach is more effective in eradicating the infection and achieving an effective end result. But despite the advantages of this method, the patient usually remains immobilized and hospitalized for a period of six to twelve weeks.

It is an object of the present invention to provide a method and apparatus for treating a hip joint infection which retains all the benefits of the two-stage joint replacement revision but which avoids the immobilization and lengthy hospitalization.

SUMMARY OF THE INVENTION

According to one aspect of the invention there is provided a method of treating an infected joint replacement which comprises the steps of removing the original hip prosthesis and fitting a temporary prosthesis, which comprises a femoral component provided with an antibiotic loaded sleeve thereon in the femoral cavity of a patient, the femoral component being designed with appropriate fatigue life and static strength based on a life of about 12 weeks of normal activity of a person recovering from a total hip replacement. In this way, the known interim infection treatment method by which a patient was rendered immobilized and hospitalized is replaced by the step of utilizing a temporary prosthesis, which is not rigidly fixed in the femoral cavity, and whilst serving to eradicate the infection, also serves the useful purpose of providing the patient with the use of the limb.

Also according to the invention there is provided a temporary prosthesis for use in the above method, comprising a femoral component which is in the form of an elongate endoskeleton having a neck portion and a stem portion adjacent to and at an angle to the neck portion, the stem portion having a proximal end which is adjacent the neck portion and a distal end which is remote from the neck portion and wherein the stem portion is of circular cross-section.

Further according to the invention there is provided a method of implanting a hip replacement in a femoral cavity which comprises the steps of inserting a mold in the form of a flexible lining into the cavity, filling the mold with a bone cement, inserting the stem of a femoral component down the femoral cavity into the bone cement, allowing the bone cement and the mold to conform to the shape of the cavity, allowing the bone cement to solidify to form a composite component comprising the femoral component and the sleeve on the stem thereof, removing the composite component from the cavity, removing the mold and reimplanting the composite femoral component in the femoral cavity.

Also according to the invention, there is provided a method of implanting an acetabular cup in the acetabular cavity of a patient comprising the steps of placing a mold of a flexible material over the acetabular cavity, placing bone cement in the mold, placing the acetabular cup in the bone cement, allowing the bone cement to set to form a composite acetabular component comprising the acetabular cup which is embedded in a mantle of bone cement which has an outer shape which conforms to the shape of the acetabular cavity, removing the mold, and reimplanting the composite acetabular component in the acetabular cavity.

According to another aspect of the invention there is provided a temporary prosthesis comprising a femoral component which is in the form of an elongate endoskeleton having a neck portion and a stem portion adjacent to and at an angle to the neck portion, which has been formed from a rod which has been bent at said angle.

Also according to the invention there is provided a freestanding composite femoral component comprising an elongate endoskeleton having a neck portion and a stem portion and wherein the stem portion is provided with an antibiotic loaded sleeve thereon which has been customized to fit the femoral cavity of a patient. According to a preferred embodiment, the sleeve is customized by molding into the femoral cavity of the patient.

According to a further aspect of the invention, there is provided a method of manufacturing a temporary prosthesis comprising a femoral component which is in the form of an elongate member having a neck portion and a stem portion and an antibiotic loaded sleeve on the stem portion, comprising the step of using the femoral cavity of a patient as a mold for shaping the sleeve.

Also according to the invention there is provided a method of manufacturing a prosthesis comprising a femoral component which is in the form of an elongate member having a neck portion and a stem portion and a sleeve on the stem portion which comprises the steps of inserting a mold in the form of a flexible lining into the femoral cavity of a patient, pouring a bone cement into the mold and allowing the mold to conform to the shape of the femoral cavity, implanting the stem of a femoral component in the cement to form a sleeve of cement around the stem of the component, allowing the cement to set to form a composite component comprising the femoral component and the sleeve around the stem of the component, and removing the composite component from the cavity and the mold. This method thus allows for the manufacture of a customized prosthesis in the operating theatre whilst the patient is undergoing the operation.

According to yet another aspect of the invention there is provided a kit for implanting a temporary prosthesis comprising a femoral component which is in the form of an elongate endoskeleton having a neck portion and a stem portion adjacent to and at an angle to the neck portion and a flexible mold for lining the femoral cavity of a patient.

Also according to the invention there is provided a kit for implanting a temporary prosthesis comprising a set of three femoral components, each of which is in the form of an elongate endoskeleton being a neck portion and a stem portion adjacent to and at an angle to the neck portion, the neck portions of the femoral components being of different lengths and a pair of femoral heads, each of which is provided with a recess for removably receiving the neck portion of any one of the femoral components, the one femoral head being capable of receiving a longer portion of the neck portion of a femoral component than the other femoral head.

Further objects and advantages of the invention will become apparent from the description of a preferred embodiment of the invention below.

BRIEF DESCRIPTION OF THE DRAWINGS

The invention will now be described, by way of examples, with reference to the accompanying drawings, in which.

DESCRIPTION OF THE PREFERRED EMBODIMENT

In the accompanying drawings, FIGS. 1 to 5 relate to aspects which are already known in the art. FIG. 1, to which reference has already been made, illustrates a known method of managing an infected total hip replacement using antibiotic loaded cement beads. FIGS. 2 to 5 illustrate different parts of permanent prostheses which are currently commercially available and to which reference will be made later on in this description.

Figure 6:
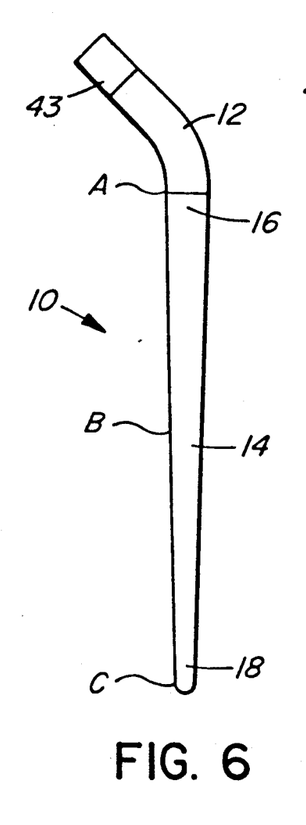
FIGS. 6 to 8 are anterior/posterior views of three different embodiments of a femoral component of a temporary prosthesis according to the present invention.

With reference to FIG. 6 of the drawings, a femoral component 10 of a temporary prosthesis according to the invention is shown. The femoral component 10 comprises an elongate endoskeleton having a neck portion 12 and a stem portion 14 adjacent to and at an angle to the neck portion 12. The stem portion 14 has a proximal end 16 which is located adjacent the neck portion 12 and a distal end 18 which is remote from the neck portion 12. The stem portion 14 is tapered from its proximal end 16 to its distal end 18. The neck portion 12 and the stem portion 14 are both circular in cross-section for ease of manufacture, but they may have any other convenient cross-section, such as rectangular or oval-shaped.

The femoral component is manufactured from a stainless steel rod which is bent at an angle to form the neck portion 12 and the stem portion 14. The rod is machined to form the taper on the stem portion 14.

Figure 7:
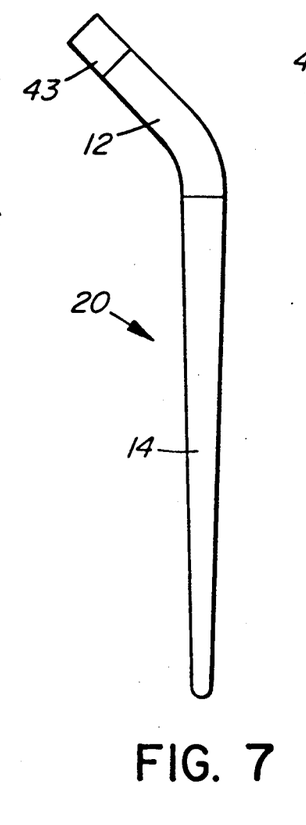
Figure 8:
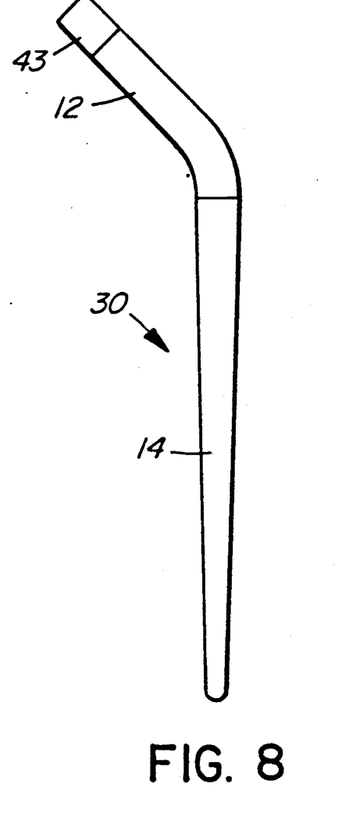

With reference to FIGS. 7 and 8, femoral components 20 and 30, similar to the component 10, but having neck portions 12 which are longer, to accommodate different patients, are shown. Suitable dimensions for the neck portions 12 for the components 10, 20 and 30 have been found to be 30 mm, 40 mm and 50 mm, respectively, as shown in the drawings. A suitable dimension for the stem portions 14 of the components 10, 20, 30 has been found to be 150 mm, as shown in FIG. 8. A suitable value for the angle δ has been found to be 135°, as shown in FIG. 8.

Figure 9:
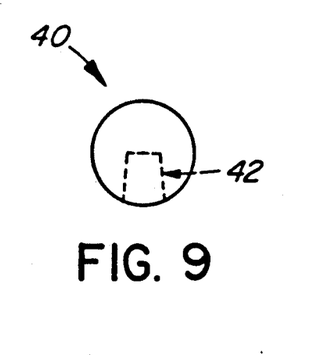
FIGS. 9 and 10 are side views of two different embodiments of a femoral head for use with the femoral components of FIGS. 6 to 8.

With reference to FIG. 9, a femoral head 40 for use with any one of the femoral components 10, 20 and 30, is shown. It is provided with a Morse taper, as shown at 42, for removably attaching it to the free end of the neck portion 12 of a femoral component 10, 20, 30, the free end of the neck portion 12 being provided with a mating formation, as shown at 43. The femoral head 40 is preferably of polished stainless steel.

Figure 10:
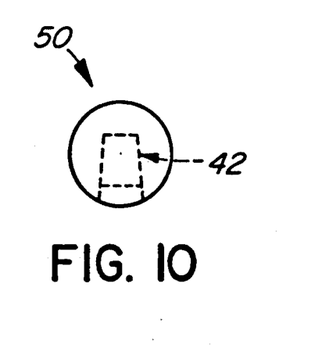

In FIG. 10, a femoral head 50 according to another embodiment of the invention is shown. The head 50 is similar to the head 40 except that it has a longer recess, which will effectively shorten the length of the neck portion 12 of the femoral component 10, 20, 30 to which it is attached. Thus, a total of six different prostheses combinations is available to fit different patients.

Figure 11:
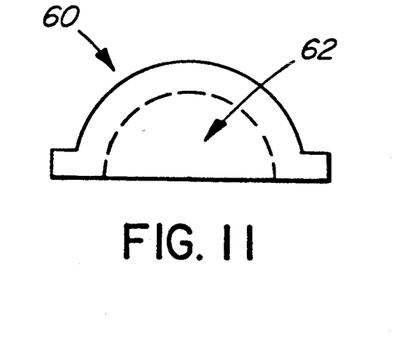
FIG. 11 is an anterior/posterior view of an acetabular cup for use with the femoral components and femoral heads of FIGS. 6 to 10.
Figure 12:
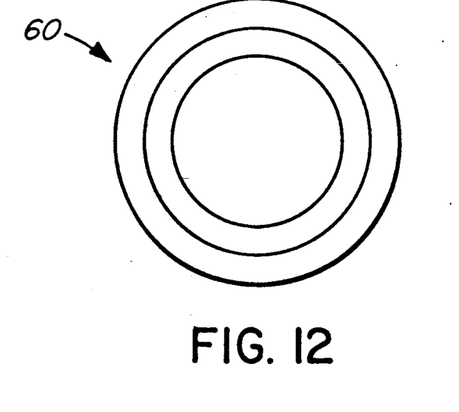
FIG. 12 is a plan view of the acetabular cup of FIG. 11.
Figure 13:
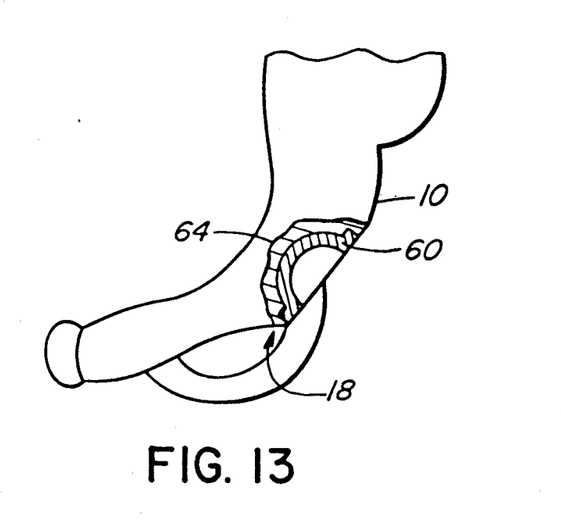
FIG. 13 is an illustration of the pelvic girdle of a patient showing the acetabular cup of FIGS. 11 and 12 located in place in the management of an infected total hip replacement using a temporary antibiotic loaded custom hip replacement according to the invention.

With reference to FIGS. 11 and 12, an acetabular cup 60 for use with the prostheses combinations of FIGS. 6 to 10 is shown. The acetabular cup 60 is provided with a semi-circular recess 62 therein for receiving the femoral head 40, 50. A suitable value for the inner radius of the recess 62 has been found to be 16 mm and a suitable thickness of the cup wall has been found to be 5 mm. The cup 60 is preferably of polyethylene.

The femoral components 10, 20 and 30 and the femoral heads 40 and 50, as well as the acetabular cup 60 are conveniently supplied together as a kit of parts.

The dimensions of the temporary components 10, 20, 30 and the acetabular cup 60 are generally smaller than the comparable dimensions of the usual permanent prostheses components. This is in keeping with the purpose of the present invention wherein the life span of the temporary femoral components 10, 20, 30 is three to six months in comparison with a ten to twenty year life span of the conventional permanent prostheses components, which are shown in FIGS. 2 to 5.

A further important difference arises with the implantation of the permanent prostheses, in cases where bone cement is used. The function of the bone cement in these applications is to bind with the bone in the femoral cavity. It primarily has a cementing function. Thus, the ratio of size of the metal component diameter to amount of bone cement is large. In the temporary prosthesis, the ratio of metal component diameter to amount of bone cement is much smaller. In the latter case the function of the bone cement is not to bind with the bone in the femoral cavity. Its function is to serve as a carrier for an antibiotic and to temporarily seat the femoral component in the femoral cavity. Thus, in this application, the metal components are not as heavy or as big. The amount of bone cement has been optimized and the amount of hardware has been minimized whereas with the permanent prosthesis, the emphasis is the other way around. The emphasis is on strength and durability of the hardware. Thus, in optimizing the amount of bone cement and minimizing the amount of hardware, the circumference of the stem portion 14 at its proximal end 16 is preferably not more than about 50 mm and the circumference at the distal end 18 preferably not more than about 25 mm. In the case of the circular component 10, 20, 30 described in the present example, therefore, the diameter of the stem portion 14 is preferably not more than about 16 mm. Likewise, the thickness of the acetabular cup 60 is preferably not more than about 5 mm.

The method according to the invention will now be described with reference to FIGS. 13 to 17 of the accompanying drawings.

Initially, the infected original hip prosthesis and all infected tissue is removed from the femur and acetabulum. An antibiotic loaded bone cement 64 is placed in the acetabular cavity 18 (FIG. 13) and the acetabular cup 60 is placed in the bone cement 64 and held in position until the cement 64 sets.

Figure 14:
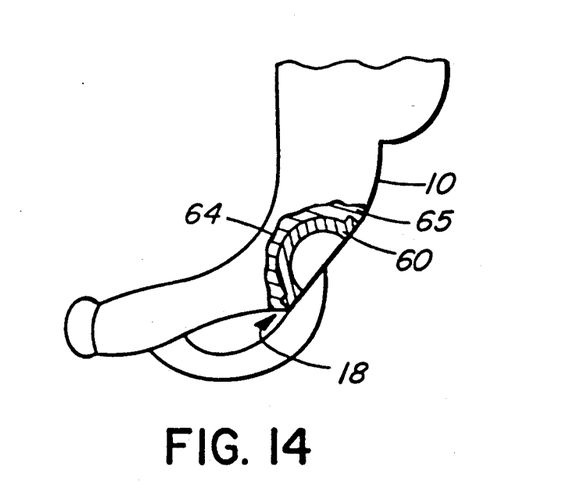
FIG. 14 is a view similar to that of FIG. 13 but illustrating the use of a latex lining as a mold to prepare a casting of the acetabular cavity of a patient, according to an alternative embodiment of the invention.
Figure 20:
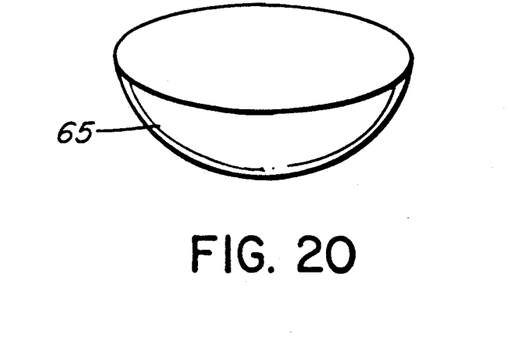
FIG. 20 is a perspective view of a flexible mold for lining the acetabular cavity of a patient.

As an alternative step, prior to placing the bone cement 64 in the acetabular cavity 18, a latex mold 65 (FIG. 20) is placed in the acetabular cavity 18. The mold 65 is flexible and conforms to the shape of the acetabular cavity 18. The bone cement 64 is placed in the mold 65 and the acetabular cup 60 is placed in the bone cement 64 and held in position until the cement 64 sets to form an acetabular composite comprising the acetabular cup 60 embedded in a mantle of antibiotic loaded bone cement 64 which has an outer shape which is a negative of the acetabular cavity 18 of the particular patient (FIG. 14). Once the cement 64 has set, the latex mold 65 is removed and the acetabular composite is reimplanted in the acetabular cavity 18.

Figure 15:
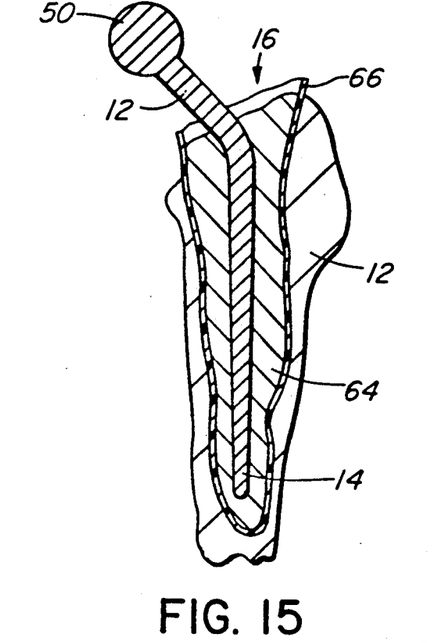
FIG. 15 is an illustration of the femur of a patient showing the molding of a sleeve of antibiotic-containing bone cement in the method according to the invention.
Figure 19:
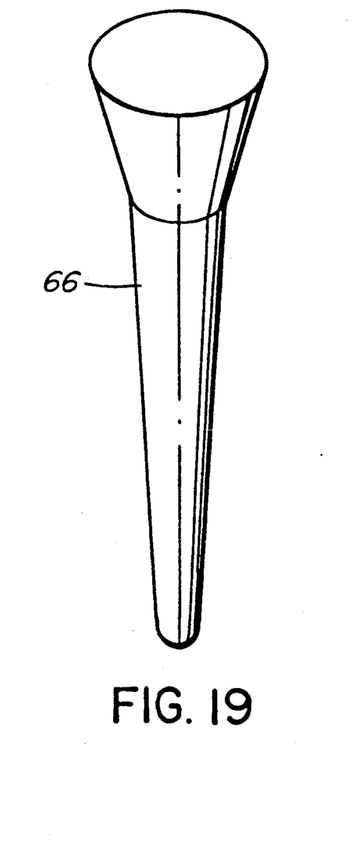
FIG. 19 is a perspective view of a flexible mold for lining the femoral cavity of a patient.

The femoral cavity 16 is broached until a conical shape is achieved (FIG. 15). The femoral component 10, 20, 30 is trialed to identify adequate neck length. A flexible latex envelope 66 (FIG. 19) is inserted into the cavity 16. Antibiotic loaded bone cement 64 is then loaded into the latex envelope 66 by means of a cement gun. The femoral component 10, 20, 30 is then inserted down the centre of the cavity 16 and the cement 64 is allowed to set. When the cement 64 has set, the composite femoral component comprising the component 10, 20, 30 and the cement sleeve 64 is pulled from the cavity 16. The envelope 66 is removed from the cement sleeve 64 which has solidified around the stem portion 14, leaving behind an accurate replica of the patient's femoral cavity 16.

To facilitate removal of the composite femoral component, two latex envelopes 66 may be used, the one being nested in the other. This is to improve relative sliding so that when the composite component is removed from the cavity 16, the one envelope 66 may remain in the cavity whilst the other comes out with the cement sleeve 64. A tool (not shown) to facilitate extraction of the composite femoral component from the femoral cavity may also be provided.

After the envelope or envelopes 66 have been removed from the femoral cavity, the composite comprising the femoral component 10, 20, 30 and the sleeve 64 is reimplanted into the cavity 16 to form a snug fit, as shown in FIG. 15.

Figure 16:
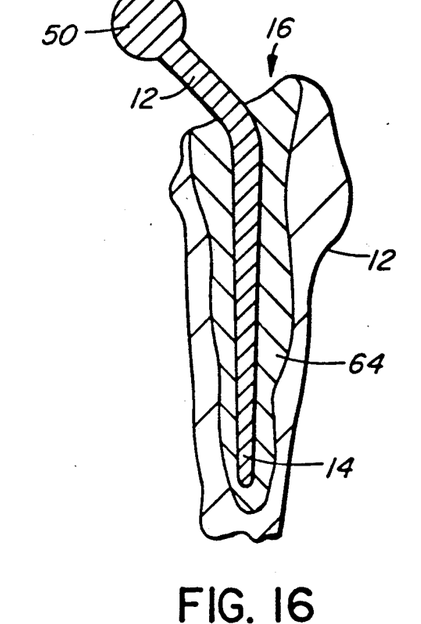
FIG. 16 is a view similar to that of FIG. 15 but showing the temporary prosthesis implanted in the femoral cavity.
Figure 17:
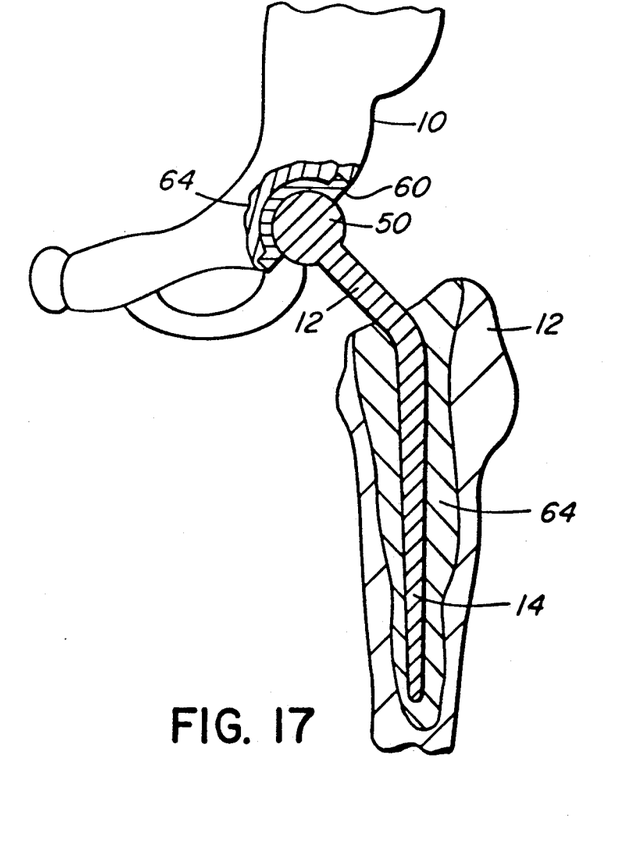
FIG. 17 is an illustration of the pelvic girdle and femur of a patient showing the femoral head reduced into the acetabular cup to form a temporary total hip replacement in the method according to the invention.

Finally, the femoral head 40, 50 is reduced into the acetabular cup 60 as shown in FIG. 16.

The antibiotic can be introduced into the bone cement in the operating theatre prior to introducing the bone cement into the acetabular and femoral cavities. Thus, the particular antibiotic used can be selected at the time of introduction based on the sensitivity of the bacteria being treated.

Figure 18:
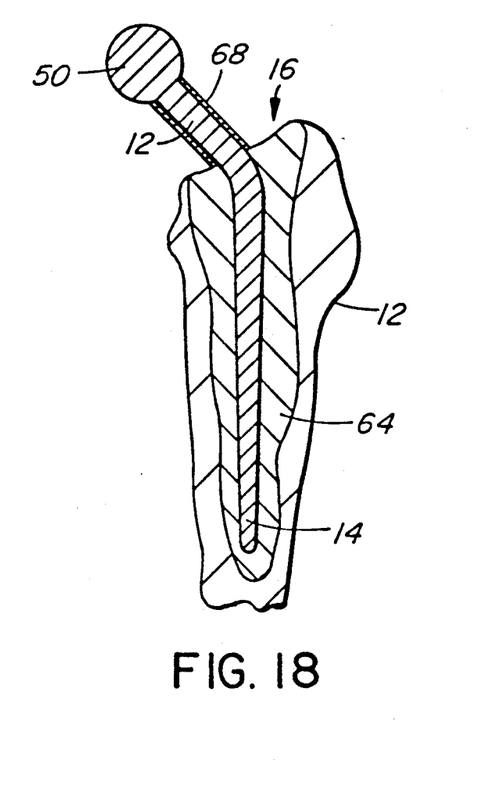
FIG. 18 is a view similar to that of FIG. 16 but showing a bone cement coating in the neck portion of the temporary prosthesis.

If desired, the neck portion 12 of the femoral component 10, 20, 30 may be coated with a layer 68 of antibiotic loaded bone cement prior to insertion into the latex mold 66 containing the antibiotic loaded bone cement 64 (FIG. 18). This is done by covering the Morse taper formation 43 with a plastic cap, dipping the neck portion 12 into the antibiotic bone cement and removing the cap before the cement hardens. This coating is applied so as not to leave metal parts exposed in a patient's body.

The latex envelope 66 serves as a container for the bone cement, as well as a mold of the femoral canal 16. The envelope 66 conveniently has the following characteristics:

(i) dimensions that fit a wide range of femoral canals
(ii) flexible enough to conform to the contours of the femoral canal
(iii) withstand the heat of polymerization of the bone cement (110 degrees Celsius max temperature)
(iv) sterilizable
(v) medical grade (i.e. able to come into contact with the femoral canal without adverse biological reaction)
(vi) strong enough to contain the bone cement
(vii) lubrication to enable the release of the femoral component with hand applied force.

The kit of parts, comprising the femoral components 10, 20, 30, the femoral heads 40, 50 and the acetabular cup 60, referred to above, conveniently further includes the other items useful for carrying out the method according to the invention, such as the flexible acetabular and femoral molds 65, 66, two unmixed bone cement packages which contain the components of the bone cement which solidify a certain period after having been mixed and an antibiotic specific for infection. Further useful items may be included in the kit, such as a cement gun nozzle, a neck adaptor to fit a conventional trial, a femoral component extractor and a plastic cap for covering the Morse taper of the neck portion of a femoral component when applying the bone cement coating around the neck portion.

The temporary prosthesis is left in position for a period of six to twelve weeks until the eradication of the infection. During this time, the patient has the use of the limb and the period of hospitalization is considerably shortened to about 14 days which is the period required for the patient to recover from the implantation of the temporary prosthesis.

Upon eradication of the infection, the temporary prosthesis is removed and a permanent hip replacement, such as those illustrated in FIGS. 2 to 5, is implanted. This implantation is by way of a conventional method. It may either be implanted by means of the application of bone cement or by means of a press-fit.

While only preferred embodiments of the invention have been described herein in detail, the invention is not limited thereby and modifications can be made within the scope of the attached claims.

What is claimed is;

1. A method of implanting a hip replacement in a femoral cavity which comprises the steps of:

inserting a mold in the form of a flexible lining into the cavity;
   filling the mold with a bone cement;
   inserting the stem of a femoral component down the femoral cavity into the bone cement;
   allowing the bone cement and the mold to conform to the shape of the cavity;
   allowing the bone cement to solidify to form a composite component comprising the femoral component and a sleeve of said bone cement on the stem thereof;
   removing the composite component from the cavity;
   removing the mold; and
   reimplanting the composite femoral component in the femoral cavity.

2. The method according to claim 1, further comprising the step of working the femoral cavity into a substantially conical shape prior to inserting the mold in the cavity.

3. The method according to claim 1, wherein the bone cement contains an antibiotic.

4. A method of implanting an acetabular cup in the acetabular cavity of a patient comprising the steps of:

placing a mold of a flexible material over the acetabular cavity;
   placing bone cement in the mold;
   placing the acetabular cup in the bone cement;
   allowing the bone cement to set to form a composite acetabular component comprising the acetabular cup which is embedded in a mantle of bone cement which has an outer shape which conforms to the shape of the acetabular cavity;
   removing the mold; and
   reimplanting the composite acetabular component in the acetabular cavity.

5. The method according to claim 4, wherein the bone cement contains an antibiotic.

6. The method according to claim 5, wherein the mold is of a latex material.

7. A method of manufacturing a prosthesis comprising a femoral component which is in the form of an elongate member having a neck portion and a stem portion and a sleeve on the stem portion which comprises the steps of:

inserting a mold in the form of a flexible lining into the femoral cavity of a patient;
   pouring a bone cement into the mold and allowing the mold to conform to the shape of the femoral cavity;
   implanting the stem of a femoral component in the cement to form a sleeve of cement around the stem of the component;
   allowing the cement to set to form a composite component comprising the femoral component and the sleeve around the stem of the component; and
   removing the composite component from the cavity and the mold.

8. The method according to claim 7, wherein the lining comprises a flexible envelope.

9. The method according to claim 7, wherein the lining comprises a pair of flexible envelopes, one of which is nested in the other.

10. The method according to claim 7, further comprising the step of coating the neck portion of the femoral component with bone cement prior to implanting the stem in the cement to form the sleeve.

11. The method according to claim 7, wherein the bone cement is impregnated with an antibiotic.

* * * * *